(12) United States Patent
Kaul

(10) Patent No.: US 8,202,924 B2
(45) Date of Patent: Jun. 19, 2012

(54) POLYTRIAZINYL COMPOUNDS AS FLAME RETARDANTS AND LIGHT STABILIZERS

(75) Inventor: Bansi Lal Kaul, Biel-Benken (CH)

(73) Assignee: MCA Technologies GmbH, Biel-Benken (CH)

( * ) Notice: Subject to any disclaimer, the term of this patent is extended or adjusted under 35 U.S.C. 154(b) by 0 days.

(21) Appl. No.: 13/271,709

(22) Filed: Oct. 12, 2011

(65) Prior Publication Data

US 2012/0071594 A1 Mar. 22, 2012

Related U.S. Application Data

(62) Division of application No. 12/435,463, filed on May 5, 2009, now abandoned.

(30) Foreign Application Priority Data

May 9, 2008 (EP) .................................. 08008717
Sep. 1, 2008 (EP) .................................. 08015381

(51) Int. Cl.
*C08K 5/3492* (2006.01)
*C07D 403/00* (2006.01)
*C08G 73/00* (2006.01)
*C08G 73/06* (2006.01)
*C08G 73/08* (2006.01)

(52) U.S. Cl. ........ 524/100; 252/609; 544/198; 544/209; 525/55; 525/418; 525/540; 528/422; 528/423; 528/424

(58) Field of Classification Search ............... 252/609; 524/100; 544/198, 209; 525/55, 418, 540; 528/422, 423, 424
See application file for complete search history.

(56) References Cited

U.S. PATENT DOCUMENTS

| 3,301,797 A | 1/1967 | Drucker et al. |
| 4,086,204 A | 4/1978 | Cassandrini et al. |
| 4,331,586 A | 5/1982 | Hardy |
| 4,504,610 A | 3/1985 | Fontanelli et al. |
| 5,919,929 A | 7/1999 | Tomei |

FOREIGN PATENT DOCUMENTS

| CH | 625814 A5 | 10/1981 |
| EP | 0357223 A2 | 3/1990 |
| EP | 0377324 A2 | 7/1990 |

OTHER PUBLICATIONS

"Triazine-Based Polymers: 4, Maldi-MS of Triazine-Based Polyamines", Dietrich Braun, et al., Polymer, vol. 37, No. 5, pp. 777-783, 1996.

*Primary Examiner* — Kriellion Sanders
(74) *Attorney, Agent, or Firm* — Norris McLaughlin & Marcus PA

(57) ABSTRACT

Compounds consisting of an oligomer or a polymer of a 1,3,5-triazine derivative, having the general formula I:

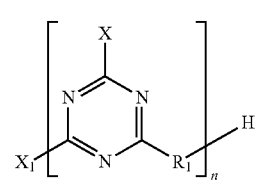

and a solvent-free process for the production of the compounds of Formula I as well as the use of the self-extinguishing oligomeric or polymeric compounds as flame retardants and light stabilizers in thermoplastic polymers such as polypropylene or regenerated cellulose or polyester.

12 Claims, No Drawings

POLYTRIAZINYL COMPOUNDS AS FLAME RETARDANTS AND LIGHT STABILIZERS

This is a divisional patent application of U.S. Ser. No. 12/435,463, filed May 5, 2009.

The present application claims priority from EP 08008717.4 filed on May 9, 2008 and EP 08015381.0 filed on Sep. 1, 2008.

The present invention relates to chemical compounds useful as flame retardants which are adapted to be incorporated into further materials, or used with further materials, e.g. synthetic polymers.

The present invention relates to chemical compounds useful as light stabilizers which are adapted to be incorporated into further materials, or used with further materials, e.g. synthetic polymers.

Water-insoluble nitrogen containing compounds, consisting of an oligomer or a polymer of a 1,3,5-triazine derivative, and having the general formula A

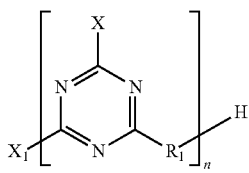

wherein X is selected from:

a heterocyclic radical containing in the ring at least one nitrogen atom which radical is linked to the triazine ring through one of such nitrogen atoms, $R_1$ is a divalent piperazine radical of the formula

a divalent radical of the type

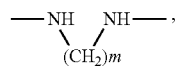

$R_2$ is alkyl or cycloalkyl, n is an integer from 10 to 30, extremes included, and m is an integer from 2 to 6,
$X_1$=halogen,
are known to the art and have been disclosed in the U.S. Pat. No. 4,504,610.

Compounds of formula A are known to impart satisfactory flame retardant properties to the thermoplastic polymers by addition of particular phosphonitrogenous additives which do not comprise aminoplastic resins and offer the advantage of, in case of fire, to prevent proliferation of fires, particularly where the plastics and coatings are involved as materials.

According to the prior art, the compounds of formula A are prepared by first reacting cyanuric acid chloride at temperatures ranging from −10° C. to +10° C., at a pH from 5 to 7, in water and in the presence of a polar solvent, such as acetone, etc. with an amine of the formula $R_2$—$NH_2$ or with a heterocyclic compound containing in the ring a nitrogen atom, in a molar ratio of 1:1, where $R_2$ has the value indicated hereinabove, whereupon the 4-amino derivative of 2,6-dichloro-1, 3,5-triazine is obtained.

Such derivative, after separation, is then reacted at elevated temperatures, in an apolar solvent, with an amine of formula $H_2N$—$(CH_2)_m$—$NH_2$ or with piperazine or an alkyl-substituted derivative thereof, or with a mixture of such compounds, employing a molar ratio between triazine derivative and amine and/or piperazine equal to 1:1.

Compounds of Formula A in wherein $R_1$ is Y which is represented in the following

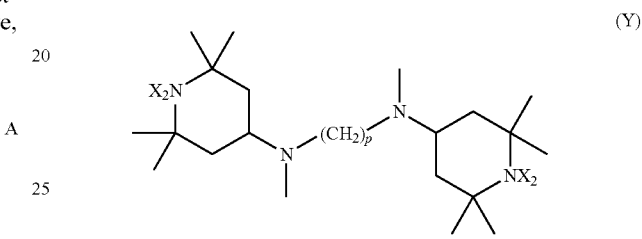

are also known to the art and are disclosed in the U.S. Pat. No. 4,086,204. Such compounds of Formula A are known to be valuable light stabilizers for synthetic polymers. The preparation of such compounds is described for example in U.S. Pat. Nos. 4,086,204, 4,331,586, 4,335,242, 4,492,791, 5,919,929, as well as in EP-A-357 223 and EP-A-377 324. Processes for the preparation of a product corresponding to the formula A wherein $R_1$=Y is may be carried out in an inert organic solvent such as acetone, dioxane, toluene, xylene, in a temperature range from −10° C. and the solvent boiling temperature; or may be carried out in a closed system under nitrogen, such as disclosed in (U.S. Pat. No. 5,919,929). The organic solvent used is preferably one or more of toluene, xylene, trimethylbenzene, isopropylbenzene, diisopropylbenzene or t-butylbenzene, especially toluene, xylene or trimethylbenzene. Xylene is especially preferred. The reaction is carried out in the presence of organic or inorganic bases for fixing hydrogen halide. Preferred examples of bases useful for said purpose are triethylamine or tributylamine, sodium hydroxide, carbonate or bicarbonate, potassium hydroxide or carbonate, sodium alcoholates The use of solvents in the synthesis of the compounds of formula A makes these processes potentially hazardous, environmentally unfriendly and expensive. Moreover, the use of solvents requires expensive equipment for their regeneration after their use.

Also, the compounds of formula A made by these certain of these prior art processes, particularly the processes described in U.S. Pat. Nos. 4,504,610 and 4,086,204) usually contain up to 2% organically bound halogen ("AOX") wherein group X of the formula A is usually a halogen atom. Thus a popular and presently commercially available flame retardant poly-2,4-piperazinyl-6-morpholinyl-1,3,5-triazine; CAS Nr.: 93058-67-4, formerly offered by Degussa AG (Germany) as "PPM-TRIAZINE" and now commercially available from AlzChem, (Germany), contains up to 1.5% organic chlorine (AOX).

Similarly the commercially available light stabilizers presently commercially available as "CHIMASORB 944", offered by Ciba Specialty Chemicals, as well as "CYASORB UV-3346" and "CYASORB UV-3529" offered by Cytec Industries Inc., (USA) can contain up to 2% organic chlorine, calculated on the basis of their average molecular weights of 1600-3000

The presence of organically bound halogen (AOX) in flame retardants and light stabilizers is desirably avoided for important environmental reasons, for safety in case of fire, for safe disposal of the waste containing such additives, and in many countries the use of flame retardants and light stabilizers comprising organically bound halogen (AOX) is presently, or may be soon legally controlled or restricted for use.

The present invention addresses and overcomes many of the shortcomings extant in the prior art.

In one aspect, the present invention relates to the halogen-free compounds of Formula I,

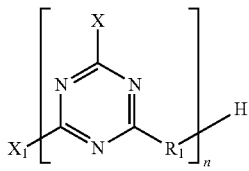

wherein X is selected from:

or, X is a heterocyclic radical containing in the ring at least one nitrogen atom which radical is linked to the triazine ring through one of such nitrogen atoms,
$R_2$ is alkyl or cycloalkyl, $R_1$ is a divalent radical of piperazine of the formula

or $R_1$ is a divalent radical according to the formula

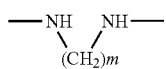

or $R_1$ may be a radical according to the formula (Y) illustrated as follows

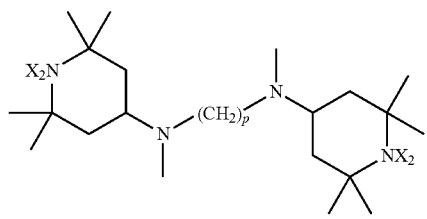

n is an integer from 2 to 30, inclusive,
m is an integer from 2 to 6, inclusive,
p is an integer from 2 to 12, inclusive,
$X_2$ is a hydrogen or an $C_1$-$C_4$ alkyl group, and $X_1$=OH, $NH_2$ or X, whereby $X_1$ and X may be the same or different.

The present invention also relates to the process of making the compounds of Formula A and of Formula I, which process proceeds preferably without the use of any organic solvents, preferably in the presence of a surface active agent.

The first step of the process according to the invention is the reaction of cyanuric acid halogenide at temperatures ranging from −10° C. to +10° C., at a pH from 5 to 7, in a polar solvent, such as acetone, water, etc. but preferably without the use of any organic solvent, with an amine of formula $R_2$—$NH_2$ or with a heterocyclic compound containing in the ring a nitrogen atom, in a molar ratio of about 1:1, preferably in a molar ratio of 1:1, to produce the 4-amino derivative of 2,6-dichloro-1,3,5-triazine, in an intermediate suspension.

Without separation, the intermediate suspension is then reacted at an elevated temperature, preferably in the range of 100° C.-200° C., within water or a polar solvent, but preferably without any organic solvent with an amine of formula $H_2N$—$(CH_2)_m$—$NH_2$, or with piperazine or an alkyl-substituted derivative thereof, or with 4-amino-2,2,6,6-tetramethylpiperidine or with N,N'-bis-(2,2,6,6-tetramethyl-4-piperidinyl)-1,6-hexandiamine, or with a mixture of such compounds, employing a molar ratio between triazine derivative and amine and/or piperazine of about 1:1, preferably in a respective molar ratio of 1:1.

The compounds of Formula I are then obtained by reacting the compounds of Formula A with a compound of the formula $HX_1$ at temperatures ranging from about 90° C. to about 150° C., more preferably at a temperature of from 100° C. to 130° C. in the presence of a base such as an excess of $HX_1$ and/or a base such as one or more alkali metal hydroxides.

A further aspect of the invention, is a process for the production of a water-insoluble oligomer or polymer of a 1,3,5-triazine derivative having the general formula:

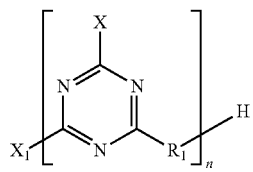

wherein X is selected from:

or a heterocyclic radical containing in the ring at least one nitrogen atom which radical is linked to the triazine ring through one of such nitrogen atoms,
$R_2$ is alkyl or cycloalkyl,
$R_1$ is a divalent radical of piperazine of the formula

or $R_1$ is divalent radical of the formula

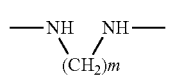

or $R_1$ is divalent radical of the formula (Y)

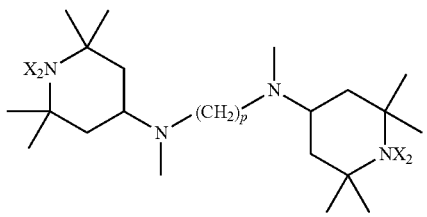

n is an integer from 2 to 30, inclusive,
m is an integer from 2 to 6, inclusive,
p is an integer from 2 to 12 inclusive,
$X_2$ is a hydrogen or a $C_1$-$C_4$ alkyl group, and
$X_1$=OH, $NH_2$ or X, whereby $X_1$ and X may be same or different,
wherein the said water-insoluble oligomer or polymer of a 1,3,5-triazine derivative is formed by condensation of a cyanuric halogenide with one or more appropriate amines and/or one or more heterocyclic compounds in two or three steps.

In order to keep the reaction mixture as a smooth suspension, it is preferable to add a surface active agent, also referred to as a tenside or surfactant, such as dodecylbenzenesulphonic acid.

The compounds according to formula I are obtained as white powders with very high melting point and having a minimal content of halogen, preferably are essentially free of halogens (namely contains less than 0.1% wt. halogens based on the weight of the said compounds) and most preferably include no halogens. They can be comminuted into to small particles which are then ready for incorporation, optionally with further flame retardant compounds, like ammonium phosphate or amine phosphate, and/or other conventional additives into synthetic polymers, especially thermoplastic polymers. The compounds according to formula I, when incorporated into or with one or more synthetic polymers to form a synthetic polymer comprising composition, provide a self-extinguishing benefit to said synthetic polymers and/or a synthetic polymer comprising compositions.

A aspect of the invention is a solvent free-process for the production of a water-insoluble oligomer or polymer of a 1,3,5-triazine derivative having the general formula:

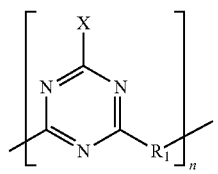

wherein X is selected from:

or a heterocyclic radical containing in the ring at least one nitrogen atom which radical is linked to the triazine ring through one of such nitrogen atoms, $R_2$ is alkyl or cycloalkyl,
$R_1$ is a divalent radical of piperazine of the formula

or a divalent radical according to the formula

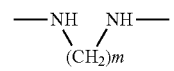

n is an integer from 10 to 30, inclusive,
m is an integer from 2 to 6, inclusive,
wherein the process comprises the step of condensation of a cyanuric halogenide with one or more amines and/or one or more heterocyclic compounds in two steps of two stages, characterized by the fact that no organic solvent is used in any of the two steps or stages The compositions of the present invention can be made according to known methods: for example, the ammonium phosphate or the phosphate of an amine are first intimately mixed with the finely ground triazine nitrogenous compound (preferably having particles sized below 75 microns) and the mixture so obtained is added to the thermoplastic polymer in a turbo-mixer to form a homogeneous mix which is thereafter extruded and preferably also granulated. The extrudate can be transformed into various articles according to any of the known art molding techniques.

The flame retardant additives of this invention are suited to be employed also in the field of fire retardant paints and fire retardant coatings.

Generally it is preferable to employ from 0.01 to 5% by weight of compounds of formula (I) or formula (A), more preferably from 0.1 to 1%, based on the total weight of the synthetic polymer comprising composition in which said compounds are included.

The compounds of formula (I) or formula (A) can be included in a polymeric material composition, viz., synthetic polymer, by various procedures, such as dry mixing in the form of powder, or by a wet process in the form of a solution or slurry. In said operation the synthetic polymer can be employed in the form of powder, granulate, solution, slurry or emulsion.

The synthetic polymers stabilized by the products of formula (I) or formula (A) can be used for the manufacture of molded articles, films, tapes, fibers, monofilaments and the like.

A mixture of compounds of formula (I) or formula (A) and synthetic polymers can optionally comprise further additives, such as antioxidants, UV absorbers, nickel stabilizers, pigments, charges, plastifying agents, antistatic agents, flame retardants, lubricating agents, anticorrosive agents, metal inhibitors, and the like.

Compounds of formula (I) or formula (A) are useful in conjunction with synthetic polymers such as, for example, high and low density polyethylene, polypropylene, ethylene-propylene copolymers, ethylene-vinylacetate copolymers, polybutadiene, polyisoprene, polystyrene, styrene-butadiene copolymers, acrylonitrile-butadiene-styrene copolymers, vinyl- and vinylidene chloride polymers and copolymers, polyoxymethylene, polyethylene-terephthalate, polyamides such as nylon 66, nylon 6, nylon 12, as well as polyurethanes, and also unsaturated polyesters. The compounds according to formula A, when incorporated into or with one or more synthetic polymers to form a synthetic polymer comprising composition, provide a self-extinguishing benefit to said synthetic polymers and/or a synthetic polymer comprising compositions.

The self-extinguishing properties of polymeric compositions containing the anti-flame additives may be evaluated as follows as follows: a thermoplastic synthetic polymer containing compounds according to formula I and/or formula A are is used to mold 3 mm (⅛ inch) thick plates in a MOORE plate press, preferably by operating the said press for about 7 minutes at a pressure of 40 kg/cm² and at a suitable temperature. The plates are subsequently removed, and allowed to cool to room temperature. Such plates are then tested according to the UL-94 method.

The polytriazine compounds of formula (I) wherein $R_1$=Y are useful and valuable agents for improving the stability to light, heat and oxidation of synthetic polymers such as, for example, high and low density polyethylene, polypropylene, ethylene-propylene copolymers, ethylene-vinylacetate copolymers, polybutadiene, polyisoprene, polystyrene, styrene-butadiene copolymers, acrylonitrile-butadiene-styrene copolymers, vinyl- and vinylidene chloride polymers and copolymers, polyoxymethylene, polyethylene-terephthalate, polyamides such as nylon 66, nylon 6, nylon 12, as well as polyurethanes, and also unsaturated polyesters.

The compounds of formula (I) wherein $R_1$=Y are also particularly useful as light stabilizers for synthetic polymers, especially polyolefins and more particularly for polyolefin articles of manufacture having a reduced thickness, such as fibers and films. Surprisingly, said compounds are only poorly leachable or extractable extracted from said thin articles, when such thin articles, e.g. films, fibers and the like, are brought in contact with water or an aqueous surfactant solution.

The compounds of formula (I) wherein $R_1$=Y can be employed as an additive for, or in a mixture with synthetic polymers in various proportions, depending on the specific synthetic polymer, the intended final use of the synthetic polymer or article formed therefrom, and the presence of additional additives.

Generally it is preferable to employ from 0.01 to 5% by weight of compounds of formula (I) wherein $R_1$=Y referred to the polymer weight, more preferably from 0.1 to 1%, based on the total weight of the synthetic polymer comprising composition in which said compounds are included The compounds of formula (I) wherein $R_1$=Y can be included in a synthetic polymeric material containing composition by various procedures, such as dry mixing in the form of powder, or by a wet process in the form of a solution or slurry. In said operation the synthetic polymer can be employed in the form of powder, granulate, solution, slurry or emulsion.

The synthetic polymers stabilized by the products of formula (I) wherein $R_1$=Y can be used for the manufacture of molded articles, films, tapes, fibers, monofilaments and the like.

A mixture of compounds of formula (I) wherein $R_1$=Y and synthetic polymers can optionally comprise further additives, such as antioxidants, UV absorbers, nickel stabilizers, pigments, charges, plastifying agents, antistatic agents, flame retardants, lubricating agents, anticorrosive agents, metal inhibitors, and the like.

The compounds of formula (I) wherein $R_1$=Y are useful in conjunction with synthetic polymers such as, for example, high and low density polyethylene, polypropylene, ethylene-propylene copolymers, ethylene-vinylacetate copolymers, polybutadiene, polyisoprene, polystyrene, styrene-butadiene copolymers, acrylonitrile-butadiene-styrene copolymers, vinyl- and vinylidene chloride polymers and copolymers, polyoxymethylene, polyethylene-terephthalate, polyamides such as nylon 66, nylon 6, nylon 12, as well as polyurethanes, and also unsaturated polyesters.

The synthetic polymers stabilized by the products of formula (I) or formula (A) can be used for the manufacture of molded articles, films, tapes, fibers, monofilaments and the like.

In the compounds according to formula (A) and formula (I), $R_2$ is preferably an alkyl radical containing from 1 to 20 carbon atoms or a cycloalkyl radical containing from 6 to 20 carbon atoms, $R_1$ is preferably a divalent radical of piperazine or a divalent radical of a diamine wherein m is an integer ranging from 2 to 6, extremes included, n preferably is an integer ranging from 8 to 20, and p preferably is an integer from 4 to 10, extremes included.

Examples of alkyl radicals are methyl, ethyl, propyl, n-butyl, isobutyl, hexyl, octyl, decyl, dodecyl, cyclohexyl, propyl-cyclohexyl, butyl-cyclohexyl, decylcyclohexyl. Examples of heterocyclic groups defined as X are morpholine, piperidine and piperazine. Examples of diamines for $R_1$ are ethylenediamine, tetramethylenediamine, pentamethylenediamine, hexamethylenediamine.

The preferred compounds of formula I are those with $R_1$=hexamethylenediamine, piperazine and alkyl-substituted piperazines as well as compounds of formula I in which $X_1$ and X are identical and have the meaning morpholino, piperidino or piperazino.

Most preferably the compounds according to formula (A), formula (I) and formula (I) wherein $R_1$=Y are halogen free, viz., do not include any halogen atoms, e.g., Br, Fl, Cl. I.

Most preferably the compounds according to formula (A), formula (I) and formula (I) wherein $R_1$=Y are water insoluble.

The following examples illustrate the preparation of several compounds according to formula A and I. All the parts indicated in such preparation are to be considered, unless otherwise specified, as parts by weight.

EXAMPLE 1

Into a reactor were charged 150 parts of water, 150 parts of ice and 0.2 parts of dodecyl-benzenesulphonic acid. Then 74 parts of cyanuric acid chloride were added under stirring over a period of 15 minutes. The mixture was stirred for 15 minutes to obtain a homogeneous suspension. After the formation of the suspension were added simultaneously 34.9 parts of morpholine and 21.2 parts of sodium carbonate (100% basis) dissolved in 150 parts of water, while maintaining the pH value between 5 and 7 and a temperature of 0-5° C. maximum. Addition time was 30 minutes. After the addition was complete, the reaction mixture was stirred at 0-5° C. for 30 minutes to form white suspension of the compound II:

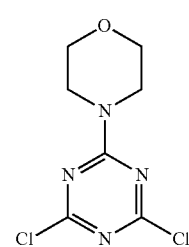

II

To the resulting white suspension of the compound II were added 34.9 parts of piperazine and the mixture heated to 40° C. and stirred at 40° C. for 30 minutes. Thereafter was added slowly over a period of 15 minutes 16 parts of sodium hydroxide (100% basis) dissolved in 100 parts of water, thereby keeping the temperature at 40° C. After stirring for 15 minutes at 40° C., the mixture was heated to 95° C. After reaching the temperature of 95° C., a second portion of 16 parts of sodium hydroxide (100% basis) dissolved in 100 parts of water was added over a period of two hours. The resulting suspension was heated for 24 hours at 130° C. under pressure and the pH at the end was basic (pH>7). The suspension was filtered at 90° C. and the product washed thoroughly with hot water till the pH was neutral. The product was dried at 100° C. for 24 hours till the weight was constant. The process yielded 109 parts of the compound of the formula

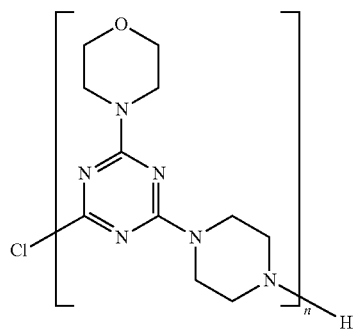

III wherein n=10, with the following characteristics:
Appearance: White powder
Melting Point: Above 290° C.
Organic chlorine content (Elemental analysis and hydrolysis method): 1.42%

EXAMPLE 2

Into a reactor were charged 150 parts of water, 150 parts of ice and 0.2 parts of dodecyl-benzenesulphonic acid. Then 74 parts of cyanuric acid chloride were added under stirring over a period of 15 minutes. The mixture was stirred for 15 minutes to obtain a homogeneous suspension. After the formation of the suspension were added simultaneously 34.9 parts of morpholine and 21.2 parts of sodium carbonate (100% basis) dissolved in 150 parts of water, while maintaining the pH value between 5 and 7 and a temperature of 0-5° C. maximum. Addition time was 30 minutes. After the addition was complete, the reaction mixture was stirred at 0-5° C. for 30 minutes, filtered, washed with water to obtain 387 parts of press cake with 23.5% solid content, corresponding to 91 parts and 96.8% of the theoretical yield of the compound of formula II. A small sample of II dried at 50° C. under vacuum has a melting point of 88.5-89° C. and an organic chlorine content of 29.8% as per elemental analysis and hydrolysis methods.

Into a 2-liter reactor equipped with stirrer, thermometer, reflux cooler and heating bath, there were introduced 1200 parts of water and 0.5 parts of dodecylbenzenesulphonic acid. Then 387 parts of the press cake of II obtained as above were added at 20° C. To the resulting white suspension were added 33.4 parts of piperazine, the mixture was heated to 40° C. and stirred at 40° C. for 30 minutes. Over a period of 15 minutes 15.5 parts of sodium hydroxide (100% basis) dissolved in 100 parts of water were added slowly, thereby keeping the temperature at 40° C. After stirring for 15 minutes at 40° C. the mixture was heated to 100° C. After reaching the temperature of 95° C., the second portion of 15.5 parts of sodium hydroxide (100% basis) dissolved in 100 parts of water was added over a period of two hours. The resulting suspension was heated for 24 hours at 125° C., the pH at the end should be basic. The suspension was filtered at 95° C. and washed thoroughly with hot water till the pH was neutral. The product was dried at 100° C. for 24 hours till the weight was constant. One obtained 97.5 parts of the compound of the formula III wherein n=10 with the following characteristics:
Appearance: White powder
Melting Point: Above 290 degree C.
Organic chlorine Content (Elemental analysis and hydrolysis method): 1.52%

EXAMPLE 3

400 parts of morpholine at room temperature were placed in a reactor with a condenser, a stirrer and a thermometer. 200 parts of the compound of Formula III (containing 1.5% chlorine) were added and the mixture heated to 120° C. The mixture was stirred for 12 hours. After cooling down to room temperature, the mixture was poured out on 1000 parts of ice and 1000 parts of water containing 3.5 parts of sodium hydroxide 100%. The resulting suspension was filtered and washed thoroughly with water at room temperature till the pH was neutral. The obtained product was dried at 100° C. for 24 hours till the weight was constant. One obtained 230 parts of the compound of the formula IIIa

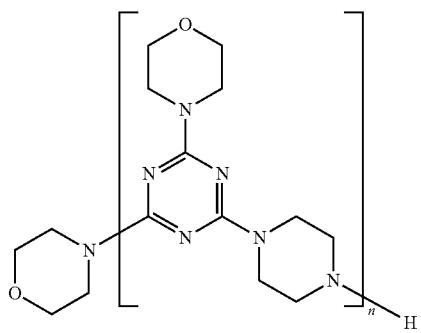

IIIa wherein n=10, with the following characteristics:
Cl content (AOX): <0.01%
Colour: White
Melting point: Above 290 C

EXAMPLE 4

40 parts of morpholine, 0.5 parts of sodium dodecylbenzenesulphonate and 1000 parts of water were placed at room temperature in a reactor with a stirrer and a thermometer. 200 parts of the compound of Formula III (containing 1.42% chlorine) were added and the mixture heated to 130° C. After stirring for 4 hours at 130° C. 3.2 parts of sodium hydroxide (100% basis) dissolved in 20 parts of water were added. The resulting suspension was heated for 8 hours at 130° C., the pH at the end should be basic. The suspension was filtered at 95° C. and washed thoroughly with hot water till the pH was neutral. The product was dried at 100° C. for 24 hours till the weight was constant. One obtained 214 parts of the compound of the formula IIIa
with the following characteristics:
Cl content (AOX): <0.01%
Colour: Off white
Melting point: Above 290 C

EXAMPLE 5

400 parts of piperazine were placed at room temperature in a reactor with a condenser, a stirrer and a thermometer. 200 parts of the compound of formula III (containing 1.72% chlorine) prepared according to example 3 of the U.S. Pat. No. 4,504,610 were added and the mixture heated to 100 C. The mixture was stirred for 12 hours. After cooling down to room temperature, the mixture was poured out on 1000 parts of ice and 1000 parts of water containing 3.2 parts of sodium hydroxide 100%. The resulting suspension was filtered and washed thoroughly with water at room temperature till the pH was neutral. The product was dried at 100C for 24 hours till the weight was constant. One obtained 203 parts of the compound of the formula IIIb

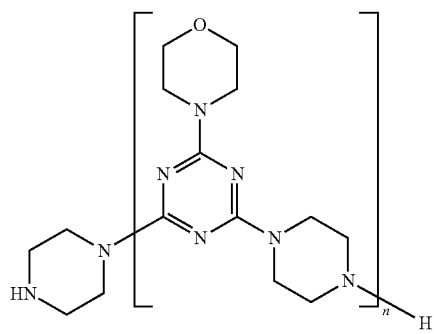

IIIb wherein n=10, with the following characteristics:
Cl content (aox): <0.01%
Colour: =Off white
Melting point: Above 290 C

EXAMPLE 6

40 parts of piperazine, 0.5 parts of dodecylbenzenesulphonic acid and 1000 parts of water were placed at room temperature in a reactor with a stirrer and a thermometer. 200 parts of the compound of Formula III (containing 1.5% chlorine) was added and the mixture heated to 130° C. After stirring for 4 hours at 130° C. 3.2 parts of sodium hydroxide (100% basis) dissolved in 20 parts of water were added. The resulting suspension was then heated for 8 hours at 130° C., the pH at the end should be basic. The suspension was filtered at 95° C. and washed thoroughly with hot water till the pH was neutral. The product was dried at 100° C. for 24 hours till the weight was constant. One obtained 237 parts of the compound of the formula IIIb

EXAMPLE 7

Using commercially available compound of Formula III [PPM-Triazine, poly-2,4-piperazinyl-6-morpholinyl-1,3,5-triazine; CAS Nr.: 93058-67-4, obtained from Degussa AG and now AlzChem, Germany, containing 1.48% organic chlorine (AOX)] in place of the compound of formula III of the Example 2 of this patent application, in example 4, the product IIIa with a yield of 97% was obtained.

The product showed the following characteristics:
Cl content: <0.01%
Colour: Off white
Melting point: Above 290 C

EXAMPLE 8

4 parts of sodium hydroxide (100% basis), 0.5 parts of dodecylbenzenesulphonic acid and 1000 parts of water were placed at room temperature in a reactor with a condenser, a stirrer and a thermometer. 200 parts of the compound of Formula III (containing 1.5% chlorine) were added and the mixture heated to 98° C. The resulting suspension was heated for 12 hours at 130° C., the pH at the end should be basic. The suspension was filtered at 95° C. and washed thoroughly with hot water till the pH was neutral. The product was dried at 100° C. for 24 hours till the weight was constant. One obtained 237 parts of the compound of the formula IIIc

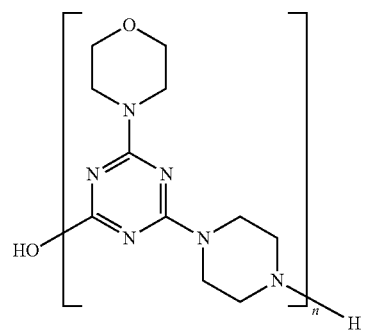

IIIc wherein n=10, with the following characteristics:
Cl content: <0.01%
Colour: White
Melting point: Above 290 C

EXAMPLE 9

Using 12 parts of ammonium hydroxide (approx 30%) in place of 4 parts of sodium hydroxide (100% basis) in EXAMPLE 8 and carrying out the reaction in a closed reactor, the compound of formula IIId was obtained

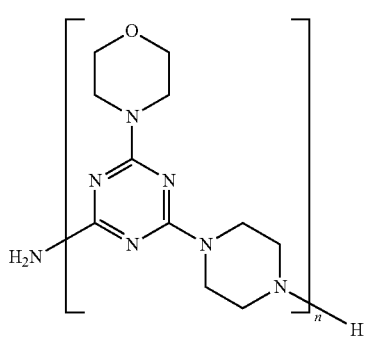

IIId wherein n=10, with the following characteristics:
Cl content: <0.01%
Colour: Off white
Melting point: Above 290 C

EXAMPLE 10

Into a reactor were charged 150 parts of water, 150 parts of ice and 0.2 parts of dodecyl-benzenesulphonic acid. Then 74 parts of cyanuric acid chloride were added under stirring over a period of 15 minutes. The mixture was stirred for 15 minutes to obtain a homogeneous suspension. After the formation of the suspension were added simultaneously 34.9 parts of morpholine and 21.2 parts of sodium carbonate (100% basis) dissolved in 150 parts of water, while maintaining the pH value between 5 and 7 and a temperature of 0-5° C. maximum. Addition time 30 minutes. After the addition was complete, the reaction mixture was stirred at 0-5° C. for 30 minutes.

To the resulting white suspension of II were added 34.9 parts of piperazine and the mixture heated to 40° C. and stirred at 40° C. for 30 minutes. Thereafter was added slowly over a period of 15 minutes 16 parts of sodium hydroxide (100% basis) dissolved in 100 parts of water, thereby keeping the temperature at 40° C. After stirring for 15 minutes at 40° C., the mixture was heated to 95° C. After reaching the temperature of 95° C., a second portion of 16 parts of sodium hydroxide (100% basis) dissolved in 100 parts of water was added over a period of two hours. The resulting suspension was heated for 24 hours at 98° C. Thereafter 5 parts of morpholine were added and the mixture was stirred for 4 hours at 120° C. (under pressure). The suspension was treated with 3.2 parts of sodium hydroxide (100% basis) dissolved in 20 parts of water at 90° C., filtered at 90° C. and the product washed thoroughly with hot water till the pH was neutral. The product was dried at 100° C. for 24 hours till the weight was constant. One obtained 101 parts of the compound of the formula IIIa with <0.1% chlorine (AOX) content.

EXAMPLE 11

Into a reactor were charged 150 parts of water, 150 parts of ice and 0.2 parts of dodecyl-benzenesulphonic acid. Then 74 parts of cyanuric acid chloride were added under stirring over a period of 15 minutes. The mixture was stirred for 15 minutes to obtain a homogeneous suspension. After the formation of the suspension were added simultaneously 34.9 parts of morpholine and 21.2 parts of sodium carbonate (100% basis) dissolved in 150 parts of water, while maintaining the pH value between 5 and 7 and a temperature of 0-5° C. maximum. Addition time 30 minutes. After the addition was complete, the reaction mixture was stirred at 0-5° C. for 30 minutes.

To the resulting white suspension of II were added 34.9 parts of piperazine and the mixture heated to 40° C. and stirred at 40° C. for 30 minutes. Thereafter was added slowly over a period of 15 minutes 16 parts of sodium hydroxide (100% basis) dissolved in 100 parts of water, thereby keeping the temperature at 40° C. After stirring for 15 minutes at 40° C., the mixture was heated to 95° C. After reaching the temperature of 95° C., a second portion of 16 parts of sodium hydroxide (100% basis) dissolved in 100 parts of water was added over a period of two hours. The resulting suspension was heated for 24 hours at 98° C. Thereafter 5 parts of piperazine were added and the mixture was stirred for 4 hours at 120° C. (under pressure). The suspension was treated with 3.2 parts of sodium hydroxide (100% basis) dissolved in 20 parts of water at 90° C., filtered at 90° C. and the product washed thoroughly with hot water till the pH was neutral. The product was dried at 100° C. for 24 hours till the weight was constant. One obtained 101 parts of the compound of the formula IIIb with <0.1% chlorine (AOX) content.

EXAMPLE 12

400 parts of water at 2° C., 400 parts of crushed ice and 0.5 parts of dodecylbenzenesulphonic acid were introduced into a 2-liter flask equipped with stirrer, thermometer, dropping funnel and cooling bath, followed by the introduction of 110.6 parts of cyanuric acid chloride over a period of 30 minutes. The mixture was stirred for 15 minutes till a homogeneous suspension was obtained. While externally cooling and maintaining the pH value between 5 and 7 and the temperature from −2° C. to +2° C., 51.6 parts of piperidine in 200 parts of water and 31.8 parts of sodium carbonate (100% basis) in 200 parts of water were simultaneously fed. The mixture was stirred for 15 minutes at 2° C. The white product thus obtained was filtered and then washed with water. There were obtained 525 parts of press cake with a solid content of 25.5% corresponding to 134 parts of the dry material corresponding to the theoretical yield of 96%.

After drying a sample of 10 parts at 50° C. under vacuum, there were obtained 2.55 parts of 2.6-dichloro-4-piperidine-1,3,5-triazine (IV) (melting point 88-88.5° C.)

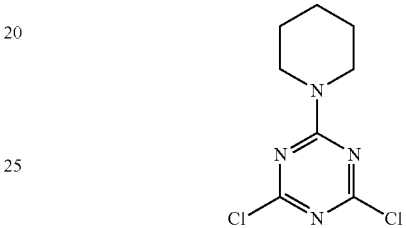

IV

The structure of such compound was proved by elemental analysis and NMR.

Into a 1-liter reactor equipped with stirrer, thermometer and heating bath, there were introduced 400 parts of water and 0.1 part of dodecylbenzenesulphonic acid. Then 46.6 parts of the product IV and 17.2 parts of piperazine were added thereto at 20° C. and letting the temperature to rise up to 30° C. due to the exothermic reaction. The mixture was heated to and stirred at 40° C. for 1 hour. Thereafter, it was heated to 130° C. under pressure and maintained at such temperature during 10 hours. 16 parts of solid sodium hydroxide 100% were successively charged and the mixture stirred at 130° C. during 10 hours. The product obtained was filtered hot, thoroughly washed with boiling water and dried. 49.2 parts of product V with a yield of 98% were obtained.

The product was insoluble in the common organic solvents and in water, its solubility values at room temperature being lower than 0.1%. It exhibited a melting point higher than 290° C. and has the following formula:

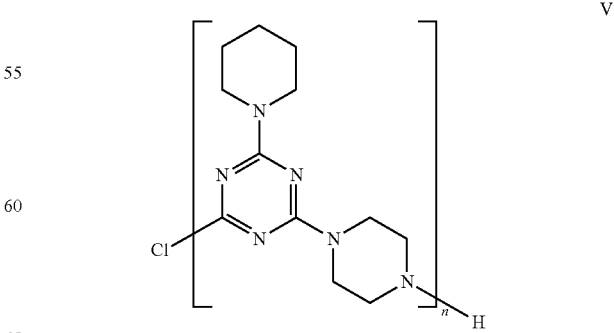

V wherein n is 10.

EXAMPLE 13

Compound Va was made by using piperidine in place of morpholine and compound V in place of compound III in example 3. It is a white powder with <0.01% chlorine (AOX) content.

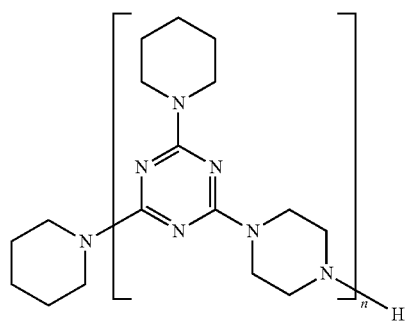

Va

EXAMPLE 14

Using 158 parts of N,N'-bis-(2,2,6,6-tetramethyl-4-piperidinyl)-1,6-hexanediamine (CAS Nr: 61260-56-7) in place of 34.9 parts of piperazine in example 1, one obtained the compound of formula VI as a white powder

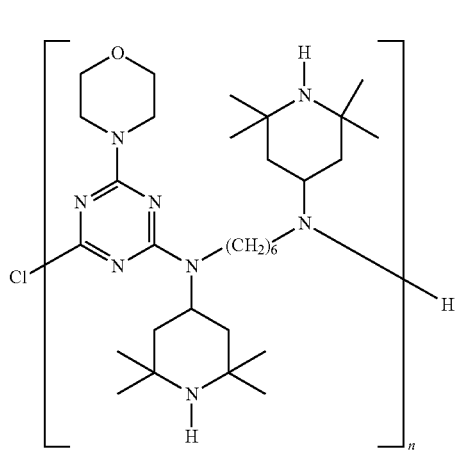

VI

EXAMPLE 15

Using 4-amino-2,2,6,6-tetramethylpiperidine instead of piperazine and the compound of Formula VI instead of the compound of formula III in Example 5 one obtained the compound of the formula VIa

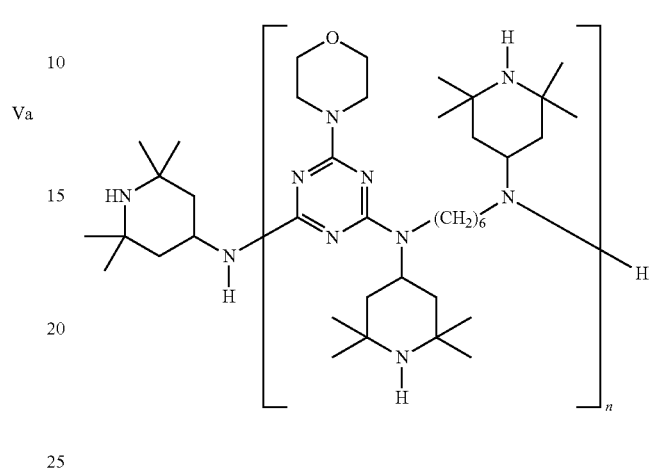

VIa

EXAMPLE 16

Using the compound of Formula VI instead of the compound of formula III in Example 3 one obtained the compound of the formula VIb

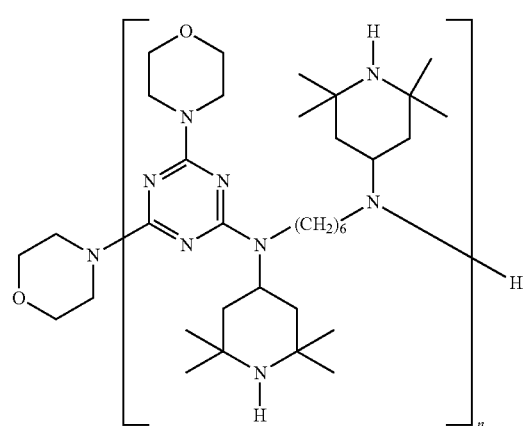

VIb

EXAMPLE 17

Using 168.8 parts of N,N'-bis-(1,2,2,6,6-pentamethyl-4-piperidinyl)-1,6-hexanediamine in place of 34.9 parts of pip erazine in example 1, one obtained the compound of formula VII as a white powder

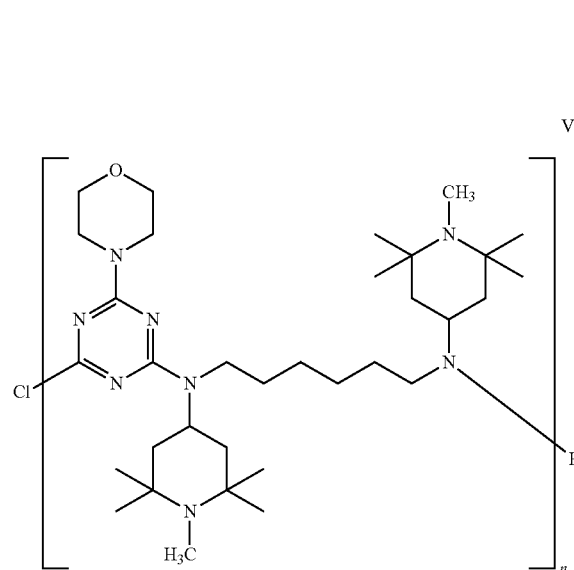

EXAMPLE 18

Using the compound of Formula VII instead of the compound of formula III in Example 3 one obtained the compound of the formula VIIa

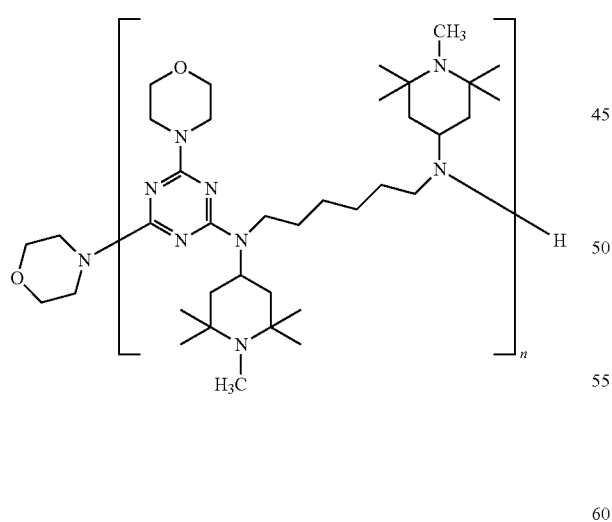

EXAMPLE 19

Using 4-amino-2,2,6,6-tetramethylpiperidine instead of piperazine and the compound of Formula VII instead of the compound of formula III in Example 5 one obtained the compound of the formula VIIb

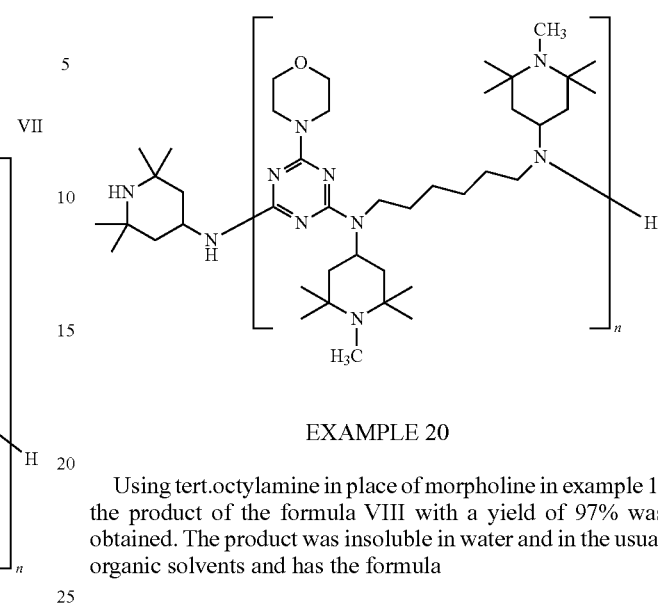

EXAMPLE 20

Using tert.octylamine in place of morpholine in example 1, the product of the formula VIII with a yield of 97% was obtained. The product was insoluble in water and in the usual organic solvents and has the formula

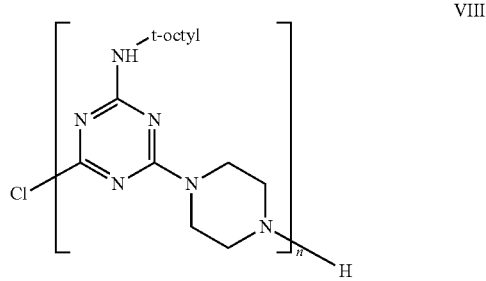

wherein n is 15.

EXAMPLE 21

Using the product of the formula VIII instead of the product of the formula III and piperidine instead of morpholine in example 4, the product of the formula VIIIa with a yield of 97% was obtained. The product was insoluble in water and in the usual organic solvents and has the formula

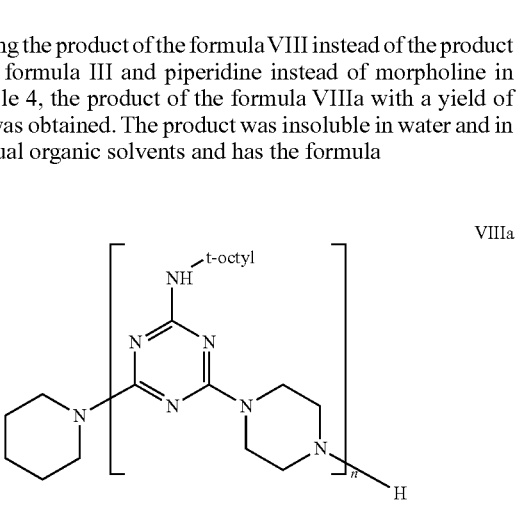

EXAMPLE 22

Using hexamethylenediamine in place of piperazine in example 12, the product of the formula IX which was insoluble in water and in the common organic solvents and wherein n is 15 was obtained.

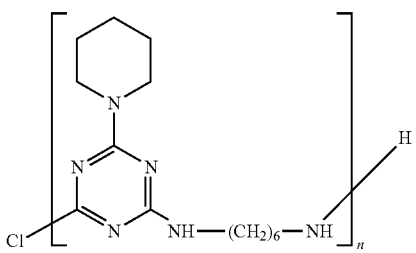

EXAMPLE 23

The product of the formula IXa was obtained by using the compound of Formula IX instead of the compound of the formula III in Example 3

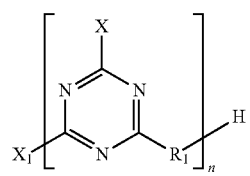

The self-extinguishing power degree can be determined by measuring the oxygen index (according to ASTM D-2863) in a Stanton Redcroft apparatus or by applying the UL-94 standards (published by "Underwriters Laboratories" USA) which provide an evaluation of the plastic materials' self-extinguishing power degree.

In the tests recorded on the following Table, for compositions containing the oligomers or polymer of formula (III), (V), (VI) and (VII) prepared according to the preceding examples, the Vertical Burning Test was employed, which permits to classify the materials at the following three levels: 94 V-0, 94 V-1 and 94 V-2, which express, in the decreasing order, the uninflammability degree. An isotactic polypropylene in flakes having a melt flow index equal to 12 was used as thermoplastic polymer.

TABLE

Self-extinguishing compositions based on polypropylene (parts of weight)

|  | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Polypropylene | 78 | 78 | 78 | 78 | 77.5 | 78 | 77 | 78 | 77.5 | 77.0 |
| Antioxidant* | 1 | 1 | 1 | 1 | 1 | 1 | 1 | 1 | 1 | 1 |
| Ammonium Polyphosphate (Exolit AP 423, Clariant) | 14 | 15 | 15 | 15 | 14 | 14 | 14 | 15 | 14 | 14 |
| Compound III | 7 |  |  |  |  |  |  |  | 7 | 7 |
| Compound IIIa |  | 7 |  |  |  |  |  |  |  |  |
| Compound IIIb |  |  | 7 |  |  |  |  |  |  |  |
| Compound IIIc |  |  |  | 6 |  |  |  |  |  |  |
| Compound IIId |  |  |  |  | 7 |  |  |  |  |  |
| Compound V |  |  |  |  |  | 7 |  |  |  |  |
| Compound Va |  |  |  |  |  |  | 7 |  |  |  |
| Compound VIIIa |  |  |  |  |  |  |  | 6 |  |  |
| Pigment Red 254 |  |  |  |  |  |  |  | 0.5 |  |  |
| Pigment Yellow 180 |  |  |  |  |  |  |  |  | 0.5 |  |
| Pigment White 6 |  |  |  |  |  |  |  | 1 |  | 1.0 |
| Oxygen Index | 27.5 | 28 | 29 | 28 | 27 | 28 | 29 | 28 | 28 | 27 |
| UL-94 at 0.8 mm | V2 | V1 | V0 | V0 | V2 | V2 | V1 | V2 | V2 | V1 |

*This is a mixture of 0.5 parts of Tris(2,4-di-tert-butylphenyl)phosphite (CAS: 31570-04-4) and 0.5 parts of Pentaerythritol-tetrakis(3-(3,5-di-tert-butyl-4-hydroxyphenyl)propionate) (CAS: 6683-19-8)

The invention claimed is:

1. An organic solvent-free process for the production of a water-insoluble halogen-free oligomer or polymer of a 1,3,5-triazine derivative according to the general formula (I):

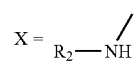

wherein X is selected from:

$$X = R_2\!-\!\overset{/}{NH}$$

or X is a heterocyclic radical containing in the ring at least one nitrogen atom which radical is linked to the triazine ring through one of such nitrogen atoms, $R_2$ is alkyl or cycloalkyl, $R_1$ is a divalent radical of piperazine of the formula

or $R_1$ is a divalent radical of the formula

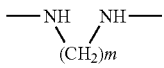

n is an integer in the range of 8 to 20,
m is an integer in the range of 2 to 6,
p is an integer in the range of 2 to 12 and,
$X_1$=OH, $NH_2$ or X, whereby $X_1$ and X may be same or different,
the process including the steps of:
  a) condensing a cyanuric halogenide with an amine of formula $R_2$—$NH_2$ or with a heterocyclic compound containing in the ring a nitrogen atom, in a molar ratio of about 1:1, to obtain the 4-amino derivative of 2,6-dichloro-1,3,5-triazine, subsequently
  b) reacting the 4-amino derivative of 2,6-dichloro-1,3,5-triazine with one or more compounds selected from: an amine of formula $H_2N$—$(CH_2)_m$—$NH_2$, or with piperazine or with an alkyl-substituted derivative of piperazine, wherein the 4-amino derivative of 2,6-dichloro-1,3,5-triazine and the one or more said further compounds are present in a molar ratio of about 1:1 and subsequently,
  c) reacting the reaction product(s) of the foregoing step with a compound of the formula $HX_1$ in the presence of a base, which base is selected from one or more of an excess of $HX_1$ or at least one alkali metal hydroxide.

2. A process according to claim 1 characterized in that no organic solvent is used in any of the three process steps.

3. A process according to claim 1 characterized in that a surface active agent is additionally present in one or more of the process steps.

4. A process according to claim 1 wherein the last process step c) is performed at a temperature(s) within the range of 90° C. to 150° C.

5. A process according to claim 4 wherein the last process step d) is performed at a temperature(s) within the range of 100° C. to 130° C.

6. A process according to claim 1 wherein $R_1$ is a divalent radical of piperazine or a divalent radical of a diamine wherein m is an integer from 2 to 6.

7. A process according to claim 1 wherein $R_1$ is hexamethylenediamine, or piperazine.

8. A process according to claim 1 wherein $R_2$ is an alkyl radical containing from 1 to 20 carbon atoms or is a cycloalkyl radical containing from 6 to 20 carbon atoms.

9. A process according to claim 1 wherein $X_1$ and X are identical and are selected from morpholino, piperidino or piperazino moieties.

10. A process for the manufacture of a self-extinguishing polymeric composition based on one or more synthetic polymers, which process includes the steps of:
  producing a water-insoluble halogen-free oligomer or polymer of a 1,3,5-triazine derivative according to the process of claim 1, and subsequently,
  incorporating the said water-insoluble halogen-free oligomer or polymer of a 1,3,5-triazine derivative into the one or more synthetic polymers.

11. The process according to claim 10 wherein the one or more synthetic polymers is an olefmic polymer or an olefinic copolymer.

12. The process according to claim 10 wherein the one or more synthetic polymers is a polyester material.

* * * * *